United States Patent
Singh et al.

(10) Patent No.: US 10,507,002 B2
(45) Date of Patent: Dec. 17, 2019

(54) X-RAY SYSTEM AND METHOD FOR STANDING SUBJECT

(71) Applicant: Siemens Healthcare GmbH, Erlangen (DE)

(72) Inventors: Vivek Kumar Singh, Princeton, NJ (US); Yao-jen Chang, Princeton, NJ (US); Birgi Tamersoy, Erlangen (DE); Kai Ma, West Windsor, NJ (US); Susanne Oepping, Erlangen (DE); Ralf Nanke, Neunkirchen am Brand (DE); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 277 days.

(21) Appl. No.: 15/602,718

(22) Filed: May 23, 2017

(65) Prior Publication Data
US 2018/0338742 A1  Nov. 29, 2018

(51) Int. Cl.
*A61B 6/00* (2006.01)
*A61B 6/06* (2006.01)
*A61B 6/08* (2006.01)

(52) U.S. Cl.
CPC .......... *A61B 6/54* (2013.01); *A61B 6/40* (2013.01); *A61B 6/42* (2013.01); *A61B 6/4417* (2013.01); *A61B 6/4464* (2013.01); *A61B 6/469* (2013.01); *A61B 6/545* (2013.01); *A61B 6/587* (2013.01); *A61B 6/06* (2013.01); *A61B 6/08* (2013.01); *A61B 6/4452* (2013.01)

(58) Field of Classification Search
None
See application file for complete search history.

(56) References Cited

U.S. PATENT DOCUMENTS

| | | | |
|---|---|---|---|
| 2013/0121468 A1* | 5/2013 | Ohta | A61B 6/4405 378/63 |
| 2015/0213646 A1 | 7/2015 | Ma et al. | |
| 2015/0228071 A1* | 8/2015 | Jockel | A61B 6/08 382/132 |
| 2016/0073979 A1 | 3/2016 | Braun et al. | |
| 2016/0092078 A1 | 3/2016 | Braun et al. | |
| 2016/0128666 A1 | 5/2016 | Grasruck et al. | |
| 2016/0213329 A1 | 7/2016 | Dirkes | |
| 2016/0262714 A1 | 9/2016 | Krauss et al. | |
| 2017/0112460 A1 | 4/2017 | Mercxx | |

OTHER PUBLICATIONS

Xtion PRO LIVE Specifications, Feb. 23, 2017, https://www.asus.com/us/3D-Sensor/Xtion_PRO_LIVE/specifications/.
Xtion PRO LIVE Overview, Feb. 23, 2017, https://www.asus.com/us/3D-Sensor/Xtion_PRO_LIVE/overview/.

(Continued)

*Primary Examiner* — Hoon K Song

(57) ABSTRACT

A system includes: a movable X-ray tube scanner; a range sensor movable with the X-ray tube scanner; an X-ray detector positioned to detect X-rays from the X-ray tube passing through a standing subject between the X-ray tube and the X-ray detector; and a processor configured for automatically controlling the X-ray tube scanner to transmit X-rays to a region of interest of the patient while the subject is standing between the X-ray tube and the X-ray detector.

16 Claims, 11 Drawing Sheets

(56) References Cited

OTHER PUBLICATIONS

Tu, Zhuowen, "Probabilistic Boosting-Tree: Learning Discriminative Models for Classification, Recognition, and Clustering" Computer Vision, 2005. ICCV 2005. vol. 2, pp. 1589-1596, Tenth IEEE International Conference on Oct. 17-21, 2005.

Ysio Max Product Brochure, 2016, Siemens.com/ysio-max.

"From ordinary to extraordinary in just one room", 2017, http://usa.healthcare.siemens.com/robotic-x-ray/twin-robotic-x-ray/multitom-rax.

* cited by examiner

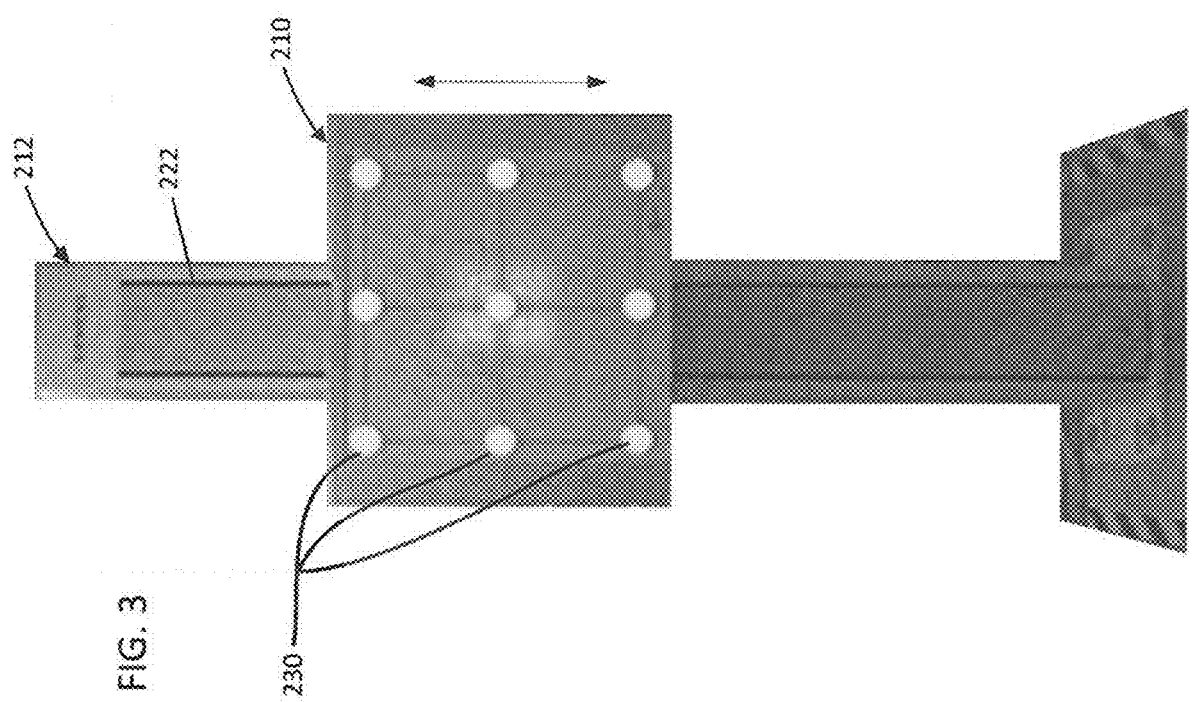

X-RAY SYSTEM AND METHOD FOR STANDING SUBJECT

FIELD

This disclosure relates to X-ray imaging systems and automated systems and methods for controlling X-ray imaging.

BACKGROUND

X-ray scanning is typically performed by a technician manually positioning an X-ray tube to focus the X-ray scan on a region of interest on a patient. The positioning and orientation of the X-ray tube with respect to the patient relies on the technician's subjective decisions, which often leads to inconsistency between different X-ray scans. X-ray scanner automation is desirable due to multiple potential benefits. In addition to improved efficiency of the scanning workflow, X-ray scanner automation may also provide better scan quality as compared with X-ray scans obtained by technicians manually positioning the X-ray tube.

SUMMARY

In some embodiments, a method comprises: receiving range data of a subject from a range sensor, where the range sensor is movable with an X-ray tube, and the subject is standing between the X-ray tube and an X-ray detector; and automatically controlling the X-ray tube to transmit X-ray radiation to a region of interest of the subject while the subject is standing between the X-ray tube and the X-ray detector.

In some embodiments, a system comprises: a movable X-ray tube scanner; a range sensor movable with the X-ray tube scanner; an X-ray detector positioned to detect X-rays from the X-ray tube passing through a standing subject between the X-ray tube and the X-ray detector; and a processor configured for automatically controlling the X-ray tube scanner to transmit X-rays to a region of interest of the patient while the subject is standing between the X-ray tube and the X-ray detector.

BRIEF DESCRIPTION OF THE DRAWINGS

FIG. 3 is a photograph of the X-ray detector of FIG. 1 during a calibration operation.

DETAILED DESCRIPTION

Figure 1:
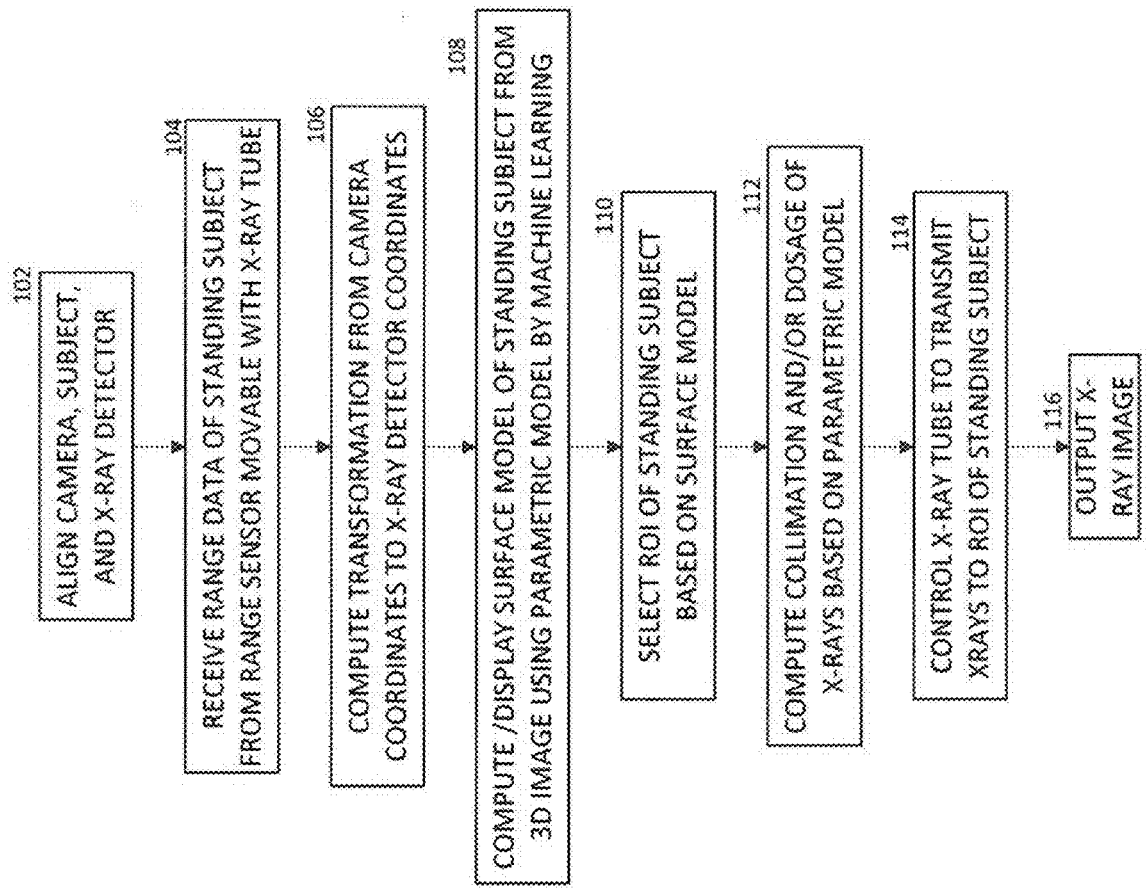
FIG. 1 is a flow chart of a method of acquiring and processing an X-ray image from a standing patient.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

This disclosure describes a system to use a 3D camera for an X-ray tube scanner automation for X-ray imaging subjects (e.g., patients) in a standing pose.

For several medical uses, it is desirable to obtain a patient X-ray with the patient in the standing pose (since the positioning of the internal landmarks and bone structure are different compared to the lying down pose). A system described below uses a 3D camera 204 for automation of X-ray tube 202 for X-ray imaging patients in standing pose. The depth image supports image analytics. The 3D camera 204 can be an infrared (IR)-based 3D sensor using IR imaging, or from a stereo camera using a pair of color/gray images. The system can be included in a new X-ray system, or can be formed by additions and/or modifications to a legacy X-ray scanning system. In some embodiments, a 3D camera 204 is mounted to be movable with an X-ray source suitable for imaging patients who are standing in front of the X-ray detector 210. The 3D camera 204 is mounted directly to the X-ray tube 202, or both are attached to another structure, so there is no relative translation or relative rotation of the 3D camera 204 with respect to the X-ray tube 202.

Figure 2A:
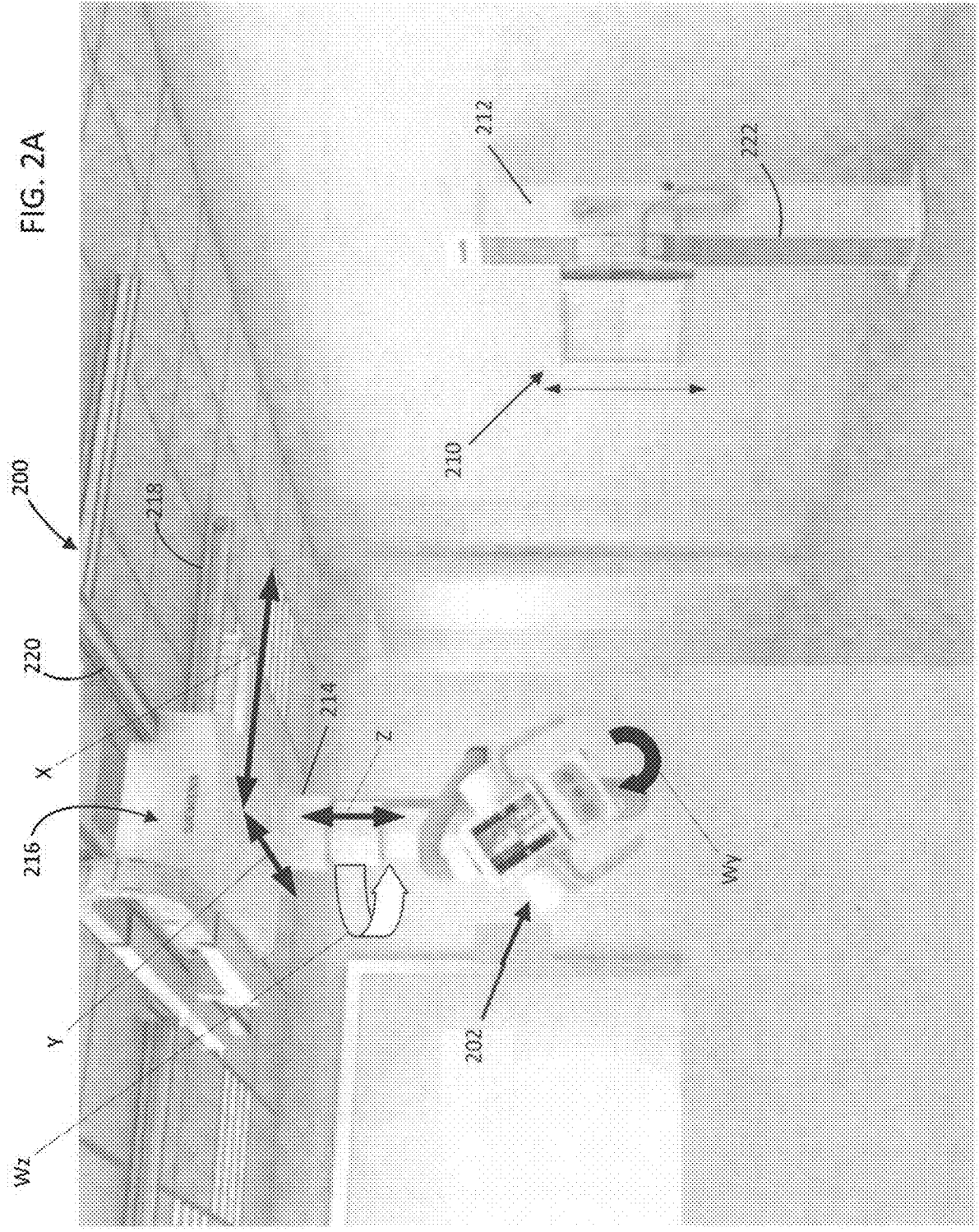
FIG. 2A is a photograph of a system according to some embodiments.
Figure 2B:
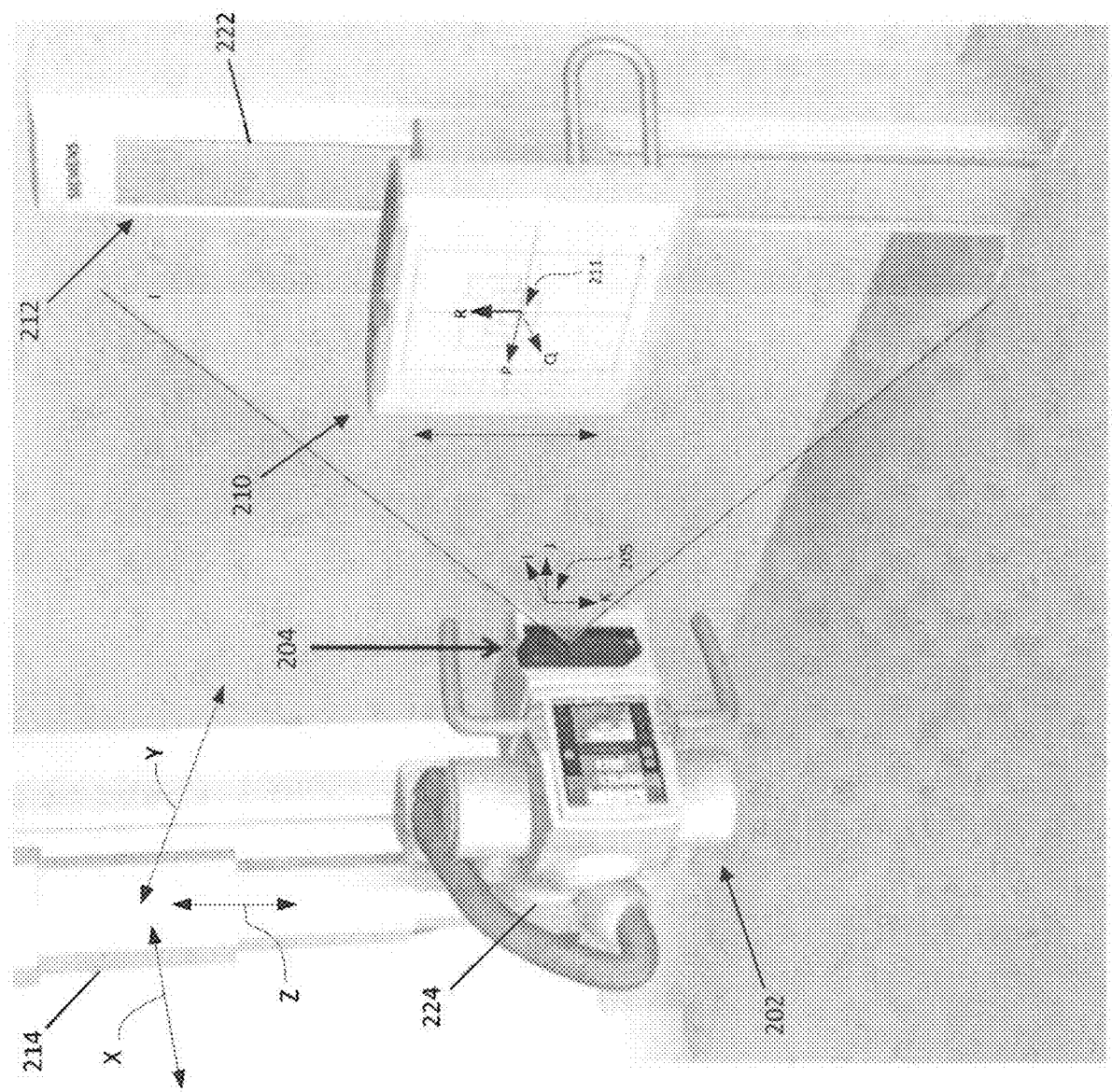
FIG. 2B is a photograph of the X-ray tube, 3D camera and X-ray detector of FIG. 1 during a calibration operation.

FIG. 2A shows an exemplary X-ray system 200. In some embodiments, the 3D camera 204 is mounted on the X-ray tube 202 as shown in FIG. 2B. Some embodiments include a calibration process (to calibrate the 3D camera 204 with the X-ray tube 202) as well as the methodology to parse a range image (also referred to as a three dimensional (3D) depth image) of a human body in order to automate the patient scanning procedure.

A 3D camera 204 mounted x-ray system with functions discussed below provides several benefits to the technician, including assisted/automated positioning of the X-ray tube 202 to align the X-ray tube 202 with the desired body region. This automated positioning avoids repeated exposures due to incorrect angles and positioning. The system can also help set the appropriate collimation for the specific body region to be scanned. In some embodiments, the technician can control the X-ray tube 202 from a remote or far away location for several scans.

Further, the detailed patient geometry can be obtained and used to set the desired X-ray dosage. The estimated 3D surface model can help determine the x-ray dose to obtain a high quality image while keeping the safety of the patient in mind. The dosage can be selected to limit the patient's X-ray exposure to a minimum amount that yields a clear X-ray image. For example, the system can select a higher dose for heavier patients or a lower dose for thin patients. For large patients a higher dose may provide better images, however too high a dose could be harmful for the patient. The system can determine the appropriate dose based on the pre-determined scanning guidelines for patient safety.

In some embodiments a 3D camera 204 is movable with the X-ray tube 202. In some embodiments, a movable X-ray tube 202 is directly attached to a movable X-ray Scanning system (not shown). In other embodiments, the X-ray tube 202 and the 3D camera 204 are both mounted to a common movable structure 216 as shown in FIG. 2B. The movable structure 216 can be mounted on a track 218 or on a track system including at least one longitudinal track 218 and at least one lateral track 220. The X-ray tube 202 is mounted to a horizontal arm 224 (FIG. 2B) which is rotatable by a first stepper motor (not shown) about its central horizontal axis. The horizontal arm 224 is in turn mounted to a telescoping vertical column 214. The telescoping vertical column 214 is rotatable about its central longitudinal arm by a second motor, and is retracted or extended by an actuator (not shown) to raise or lower the X-ray tube 210.

The system 200 includes an X-ray detector 210 which is movably mounted on a stand 212. The stand 212 is relatively fixed; i.e., the stand 212 can be fixed (e.g., bolted) to the floor of the room containing the system 200. The stand 212 can remain in this fixed position indefinitely, until the room is repurposed or the X-ray detector 210 is removed or replaced. The X-ray detector 210 is configured to be actuated up and down on a track 222 by a stepper motor (not shown) under automatic control.

In an example according to some embodiments, a 3D camera 204 is added to an X-ray scanning system such as the "YSIO MAX"™ system by Siemens AG of Berlin, Germany, and the X-ray detector 210 and control program hardware and/or software are replaced.

The system 200 allows assisted or automated positioning of the X-ray source (X-ray tube 202) to align with the desired body region of interest (ROI). Positioning accuracy, collimation accuracy and dosage accuracy are improved. This allows the technician to avoid repeatedly exposing the patient to X-rays during repeat imaging of the ROI due to incorrect angles. The system 200 can help set the appropriate collimation automatically. When the technician is tasked to take several scans, the system 200 allows the technician to control the X-ray tube 202 from a remote or far away location. The detailed patient geometry can be obtained, and the patient surface model can be used to set the desired X-ray dosage.

The estimated 3D surface model can help determine the x-ray dose to obtain a high quality image while keeping the safety of the patient in mind. For large patients a higher dose may provide better images, however too high a dose would be harmful for the patient. System can determine the appropriate dose based on the pre-determined scanning guidelines for patient safety.

Sensor Placement

With a 3D camera 204 mounted to move with the X-ray tube 202 (instead of a fixed position at the ceiling), the 3D camera 204 has a similar field of view (FOV) to the FOV of the X-ray tube 202 and is not occluded by the X-ray tube 202.

Embodiments of the exemplary system generate a personalized 3D mesh model of a subject (e.g., a person) that estimates the detailed body pose as well as the shape of the person from the range image data (referred to below as "3D depth image") obtained from a depth camera, such as a "KINECT"™ camera sold by Microsoft Corporation of Redmond, Wash. Such a personalized 3D mesh model of a person is referred to herein as an avatar. Some embodiments of the present system generate a personalized mesh using a single snapshot from a 3D camera 204 that captures a partial view of the person wearing clothing. Embodiments of the present system can reconstruct a detailed body shape (mesh), even from a partial view of the body. Various embodiments estimate body shape from a single snapshot using any type of depth camera sensor (e.g., visible or infrared), regardless of whether the person is wearing clothing. Some embodiments of the system use appropriate sensor noise statistics modeling to obtain precise body pose and shape.

3D cameras 204 provide depth information along with typical image information, such as RGB (Red, Green, Blue) data or near infrared (NIR). A 3D camera 204 can be a structured light based camera (such as Microsoft "KINECT"™ or "ASUS XTION"™ sold by AsusTeK Computer, Inc. of Taipei, TW), a stereo camera, or a time of flight camera (such as "SENZ3D" camera sold by Creative Technology Ltd of Singapore). The image data obtained from a depth camera is referred to as a 3D depth image, in which the value of each pixel corresponds to a depth or distance of the pixel from the 3D camera 204.

Some embodiments use a 3D camera 204 for X-ray tube 202 scanner automation, and a machine learning-based method to localize body landmarks in a 3D depth image obtained using the 3D camera 204. Some embodiments use the 3D camera 204 mounted on an X-ray tube 202 to acquire the 3D depth image data. Due to the mobility of the X-ray tube 202, embodiments of the present system include a calibration between the coordinate systems of the 3D camera 204 and the X-ray detector 210.

FIG. 1 illustrates a method for X-ray tube 202 scanner automation according to some embodiments. The method of FIG. 1 transforms 3D depth image data of a patient to generate a patient model and performs automated positioning of an X-ray tube 202 to acquire X-ray images of an ROI of the patient.

Figure 4:
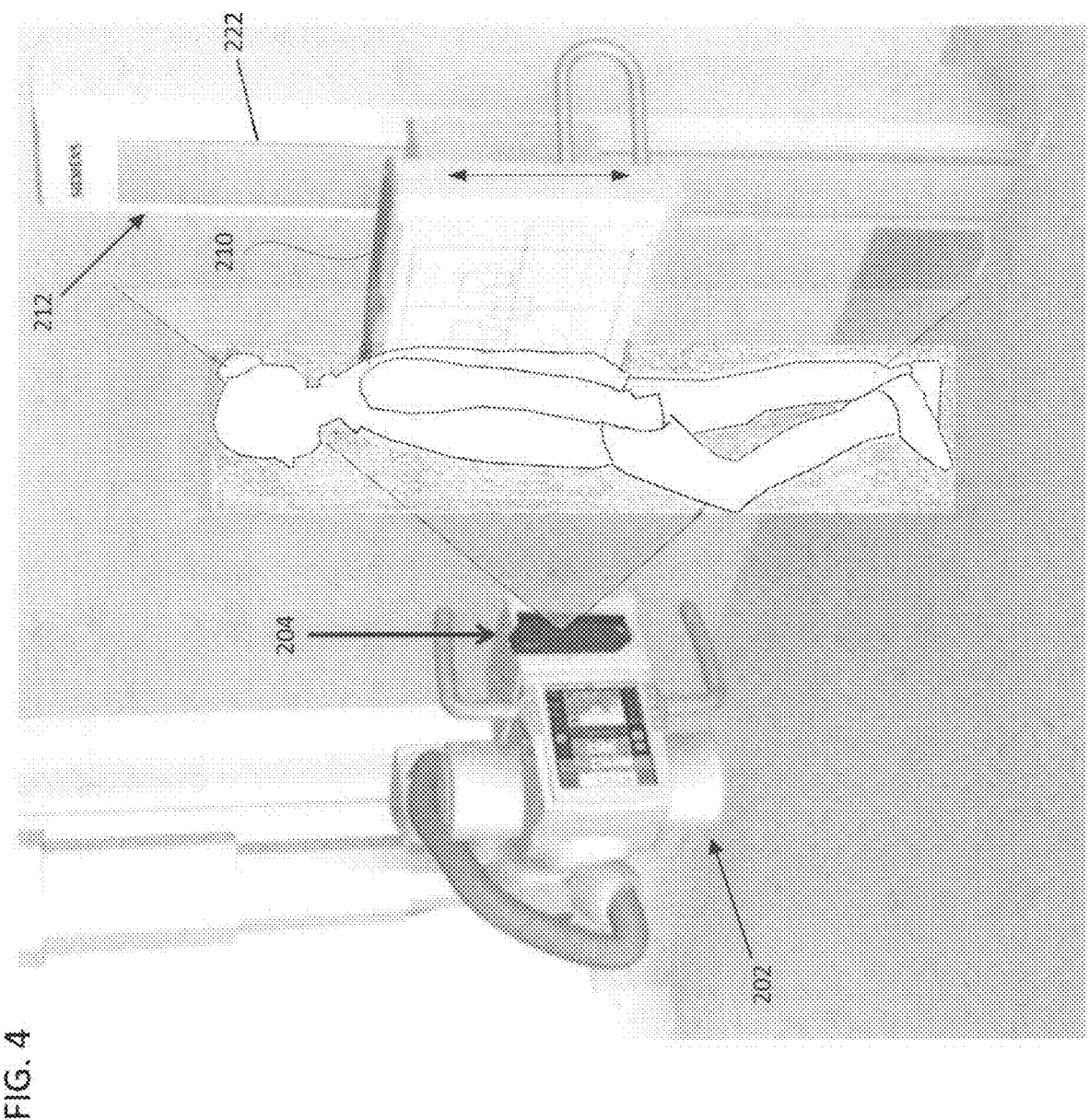
FIG. 4 is a schematic diagram of the system of FIG. 2B collecting an image of a patient.

At step 102, the user (e.g., technician) aligns the 3D camera 204, patient and X-ray detector 210 by positioning the patient standing in between the 3D camera 204 and the X-ray detector 210, with the patient either standing facing the 3D camera 204 or standing with his/her back facing the 3D camera 204, as best seen in FIG. 4.

At step 104, once the patient is positioned between the X-ray tube 202 and the X-ray detector 210, a 3D depth image of the patient is acquired using the 3D camera 204. A control is actuated (e.g., a button is pushed, an icon on a touch screen is touched, or the like) to initiate movement of the X-ray tube 202. The X-ray tube 202 then moves to a pre-determined location with a coarse precision, such that the 3D camera 204 image plane is parallel to the X-ray detector 210. Such a position is determined during the calibration process of the system discussed in the description of FIG. 2B. While the subject (patient) stands still, the operator actuates a control to trigger an image acquisition using the 3D camera 204. In some embodiments, the system then uses image analytics to obtain a detailed patient model. In some embodiments, an estimated patient model is displayed on the console/screen. Details of the analytics are discussed below in the description of FIG. 7. The 3D camera 204 receives 3D depth image data of the patient standing between the 3D camera 204 and the X-ray detector 210. In some embodiments, the 3D Depth image is acquired in response to an input received from user (e.g., a technician), such as the user pressing a trigger button or touching a control on a touch screen.

In some embodiments, the technician selects the ROI for the scan, such as the subject's left knee. In other embodiments, the system automatically selects the ROI. In some embodiments, the system suggests a set of scan protocol details (such as the collimation region, dose parameters or the like.) In some embodiments, the X-ray tube 202 is automatically moved to a predetermined location prior to acquiring the 3D depth image using the 3D camera 204 mounted on the X-ray tube 202. For example, the X-ray tube 202 can be centered relative to a height of about one meter above the floor to ensure that the patient is in a field of view of the 3D camera 204. This can be a coarse movement and the X-ray tube 202 need not be positioned in a precise location or with a particular orientation, as the 3D depth image of the patient has been calibrated to the coordinate system 211 of the X-ray detector 210. The X-Ray Detector coordinate system 211 refers to the coordinate system with its origin and axes defined by the X-Ray detector and detector stand. In other embodiments, the depth image is acquired without first moving the X-ray tube 202 to a predetermined location. In this case the system determines whether one or more predetermined landmark types are visible in the 3D depth image for the depth image to be registered to the coordinate system 211 of the X-ray detector 210. If not, the X-ray tube 202 can be re-positioned and another 3D depth image can be acquired.

At step 106, a transformation between an (I, J, K) coordinate system 205 of the X-ray tube 202 and a (P, Q, R) coordinate system 211 of the X-ray detector 210 is calculated. In some embodiments, the transformation between the (I, J, K) coordinate system 205 of the X-ray tube 202 and the (P, Q, R) coordinate system 211 of the X-ray detector 210 is estimated by the transformation between the coordinate system 205 of the 3D camera 204 and the coordinate system 211 of the X-ray detector 210 (because the 3D camera 204 is fixedly mounted to translate and/or rotate with the X-ray tube 202).

At step 108, a patient model is computed from the 3D depth image. FIGS. 5-10 illustrate a method for generating a patient model from a 3D depth image of a patient according to an embodiment of the present system and method. The method of discussed below with respect to FIG. 5 can be used to implement step 108 of FIG. 1.

At step 108, the patient model generated from the 3D depth image is displayed. For example, the patient model can be displayed on a display screen of a computer or on a console of the X-ray scanner itself. The displayed patient model can show the re-projected image of the patient labeled with the detected body regions. The patient model can show boxes or cross points representing the positions of the detected landmarks. Alternatively, the displayed patient model can show a human skeleton model representing the patient's body.

At step 110, a user (or automatic) selection of a region of interest on the displayed patient model is received. For example, the user (e.g., technician), can select the region of interest of the patient by clicking on a target portion of the displayed patient model using a mouse, touchscreen, etc.

At step 112, the system computes the X-ray collimation (FOV) and/or the X-ray dosage based on the parametric model.

At step 114, the X-ray tube 202 is automatically controlled to acquire the X-ray image of the region of interest.

In particular, the position and orientation of the X-ray tube 202 is automatically controlled to align the X-ray tube 202 with the selected region of interest. In one embodiment, the X-ray tube 202 can be automatically guided to be aligned with the selected ROI because the relationships between the coordinate systems of the X-ray tube 202, the 3D camera 204, and the X-ray detector 210—(P, Q, R), 205 and 211, respectively—were established using the X-ray tube 202 position control parameters of a control system of the X-ray tube 202. Once the X-ray tube 202 is aligned with the selected ROI, one or more X-ray images are acquired of the region of interest using the X-ray tube 202.

To carry out the X-ray tube scanner automation, the 3D positon of the target region of interest is transferred from the 3D camera 204 coordinate system 205 to the X-ray tube coordinate system (I, J, K). According to an advantageous embodiment of the present system and method, inverse kinematics can be applied in order to determine joint angles and tube base positions for the X-ray tube control. To this end, kinematic calibration is used to establish a transformation between the 3D camera 204 and the kinematic chain of the X-ray tube control system. As describe above, this kinematic calibration can also be used in step 102 of FIG. 1 to calculate the transformation between the coordinate system 205 of the 3D camera 204 and the coordinate system 211 of the X-ray detector 210.

Returning the FIG. 1, at step 116, the X-ray image is output. The X-ray image can be output by displaying the X-ray image on a display screen of a computer system, printing a physical copy of the X-ray image, and/or storing the X-ray image in memory or storage of a computer system.

As shown in FIG. 2A, the X-ray scanning apparatus includes and an X-ray tube 202 and an X-ray detector 210. The X-ray tube 202 has at least five degrees of freedom (translations in three directions, and rotations at least about the pitch and yaw axes of the X-ray tube 202) to move with respect to the X-ray detector 210 and the patient standing in front of the patient X-ray detector 210. This allows the X-ray tube 202 to move to different positons and orientations to capture x-ray images of target regions of interest (ROI) of a patient in front of the X-ray detector 210. As shown in FIG. 2B, a 3D camera 204 is mounted on the X-ray tube 202. In FIG. 2B, the camera is mounted on the front side of the tube. In other embodiments (not shown), the camera is mounted on the rear side and would not be visible from the viewpoint of FIG. 2B. The placement of the camera relative to the X-ray tube 202 can be varied among locations, such that the patient and/or stand 212 can be inside the field of view the 3D camera 204 when the X-ray tube 202 is placed on the preset location.

For example, the 3D camera 204 can be attached to a rear side of the X-ray 202, but the present system and method is not limited thereto. A computer, such as the computer shown in FIG. 8 and described below, communicates with the X-ray tube 202 and the 3D camera 204 to control the operations of the X-ray tube 202 and the 3D camera 204.

FIG. 2A illustrates motions of the X-ray tube 202 according to an embodiment of the present system and method. As shown in FIG. 2A, based on the mechanical specification of the X-ray tube 202, there are at least five parameters for tube motion control including three translational parameters: TubeLongitudinal (X), TubeTransverse (Y), and TubeLift (Z) and two rotational parameters (RotVertical (Wz) and RotHorizontal (Wy). As best seen in FIG. 2A, the three translation vectors are orthogonal, and the two rotational parameters Wz and Wy have different axes of rotation.

As shown in FIG. 2B and discussed above, the 3D camera 204 can be attached to a rear side of the X-ray tube 202. This contributes an additional six degrees of freedom transform between the 3D camera coordinate system 205 with respect to the X-ray tube 202/collimator coordinate system (I, J, K). The 3D camera coordinate system 205 refers to the local coordinate system with its origin and axes defined by the 3D camera. The X-ray tube collimator coordinate system (I, J, K) refers to the coordinate system 205 with its origin and axes based on the X-ray tube 202. The origin and axes of coordinate system 205 change whenever the position and orientation of the X-ray tube 202 changes. As the X-ray tube 202 is not within the 3D camera's field of view, a calibration target can be used to establish a link between the 3D camera coordinate system 205 and the X-ray tube coordinate system (I, J, K). As discussed above, the targets can be robustly detected and identified for camera pose estimation with respect to the coordinate system 211 of X-ray detector 210. This allows use to close the loop of kinematic chain of X-ray tube control.

With the X-ray tube 202 positioned, the operator triggers the X-ray scan by selecting a control (not shown) e.g., pressing a "Scan" button on the console.

Once the calibration is performed, the 3D depth image corresponding to each respective position of the X-ray tube 202 can be used to locate the patient with respect to the system. There is no need to repeat this calibration, as long as the stand 212 holding the X-ray detector 210 does not move. Controlled up and down motion of the X-ray detector 210 (with respect to the stand 212) and movement of the X-ray tube 202 are both accommodated without the need for a re-calibration.

In some embodiments, tube position control parameters of a control system of the X-ray tube 202 are received, and the transformation between the coordinate system 205 of the 3D camera 204 and the coordinate system 211 of the X-ray detector 210 is calculated using a kinematic calibration based on the X-ray tube 202 position control parameters of the control system of the X-ray tube 202. This embodiment enables automated control of the X-ray tube 202 without the need for detecting any targets.

In some embodiments, the X-ray tube 202 position control parameters (FIG. 2A) can include three translational parameters and two rotational parameters to control a position and orientation of the X-ray tube 202. The X-ray tube 202 position control parameters corresponding to a current position and orientation of the X-ray tube 202 can be received from the control system of the X-ray tube 202 and used in the kinematic calibration. The kinematic calibration calibrates the coordinate system 205 of the 3D camera 204 with the coordinate system 211 of the X-ray detector 210 and coordinate systems (I, J, K) of a kinematic chain of the X-ray tube 202 control system. The kinematic calibration is described in greater detail below.

Calibration

One challenge of mounting the 3D camera 204 on the X-ray tube 202 is that the 3D camera's position with respect to the tube collimator coordinate system is not known in advance. Another challenge with the movable X-ray detector stand 212 is that its location with respect to the scanning room coordinate system does not remain constant from one scanner room to another. In some embodiments, a calibration operation is performed any time the stand 212 of the X-ray detector 210 is installed or moved as well as any time the 3D camera 204 is installed or moved relative to the X-ray tube 202. In some embodiments, the calibration is done by placing circular reflective markers 230 on the surface of the X-ray detector 210 as shown in FIG. 3. The calibration includes acquiring at least one 3D depth image using the 3D camera 204 with the collimation of the X-ray tube 202 aligned with the X-ray detector 210. For IR-based 3D camera, the reflective markers are visible in the raw IR image acquired from the 3D camera. For stereo-based 3D camera, the reflective markers can be detected from the images acquired from the stereo camera. For example, a Hough transform can be applied to the raw IR image to detect visible circular targets 230. The Hough transform uses gradient information extracted from the image and detects circular shapes in the image based on the gradient information. The 3D location of the reflective markers can be estimated in the camera's coordinate system 205 based on the detected marker positions. Therefore, the transformation between camera's coordinate system 205 and the detector coordinate system 211 can be established. As the collimation is aligned with the detector during the calibration phase, the transformation between camera's coordinate system 205 and coordinate system of the collimation can be derived from the transformation between camera's coordinate system 205 and the detector coordinate system 211.

FIG. 2B shows the system 200 performing a calibration process. The calibration associates the 3D camera coordinate system 205 of the 3D camera 204 with the X-ray tube coordinate system (I, J, K) of the X-ray tube 202. When the association is established through the kinematic chain of the X-ray tube control system, the X-ray tube 202 is automatically guided, so its collimator center is focused on any point of interest in the 3D camera coordinate system 205. In the case of a standing pose scan, the coordinate system 211 of the X-ray detector 210 is used as the reference coordinate system, as a patient always stands in front of the detector 210 and her/his body surface is aligned with the detector surface orientation.

Therefore, the task of calibration is turned into finding two fixed but unknown transformations:

(1) $M_{CL}$: the transformation from the 3D camera coordinate system 205 to the X-ray tube collimator coordinate system. The transformation can be described with a 4×4 matrix:

$$\begin{bmatrix} R_{CL} & t_{CL} \\ 0 & 1 \end{bmatrix}, \quad (1)$$

where the $R_{CL}$ is a 3×3 rotation matrix from the axis of the FOV of the 3D camera 204 to the axis of the axis of the FOV of the X-ray tube 202, and $t_{CL}$ is a 3×1 translation vector from the centroid of the 3D camera 204 to the centroid of the X-ray tube 202, and 0 is a 1×3 vector with zeros. As the 3D camera 204 is attached to the X-ray tube 202, this transformation is fixed and can be derived from the calibration.

(2) $M_{DG}$: the transformation from the detector coordinate system 211 to the global tube coordinate system (X, Y, Z). The global tube coordinate system refers to the X-ray base coordinate system. The global tube coordinate system's origin and axes do not change once the X-ray system is installed in the scanning room (until the whole X-ray system is moved or reinstalled). The transformation can also be described with a 4×4 matrix:

$$\begin{bmatrix} R_{DG} & t_{DG} \\ 0 & 1 \end{bmatrix}, \quad (2)$$

where the $R_{DG}$ is a 3×3 rotation matrix, $t_{DG}$ is a 3×1 translation vector, and 0 is a 1×3 vector with zeros. As the detector stand 212 is fixed when it has been installed in the scanning room, the transformation is also fixed and can be derived from the calibration.

These two transformations can be estimated with multiple observations of the detector 210 at various known tube positions. More formally, a point $P_D$ in the detector coordinate system 211 can be transferred to the global tube coordinate system (X, Y, Z) by two paths:

$$P_G = M_{LG} M_{CL} M_{DC} P_D = M_{DG} P_D, \quad (3)$$

where $M_{DC}$ is the transformation from the detector coordinate system 211 to camera coordinate system (I, J, K), which can be derived from the observed detector landmarks in the acquired images, and $M_{LG}$ is transformation of the tube control system governed by the tube control parameters that transfers a point in the tube collimator coordinate system to the global tube coordinate system (X, Y, Z).

In some embodiments, the transformation $M_{DC}$ is estimated from a set of K landmarks 230 (FIG. 3) on the detector 210, $\{P_D^k\}$, at a predefined height and the corresponding 2D projections on the 3D camera image, $\{p_C^k\}$, by minimizing the 2D re-projection errors:

$$M_{DC}^* = \operatorname{argmin}_{M_{DC}} \Sigma_k \| f_C(M_{DC} P_D^k) - p_C^k \|^2, \quad (4)$$

where $f_C(.)$ is a 3D to 2D projection function that projects a 3D point in camera's coordinate system 205 to its image plane. In one embodiment for the Siemens Ysio system, the nine-line intersection points are used for the landmarks (FIG. 3). As the landmarks 230 are coming from a planar surface, the transformation $M_{DC}$ can be estimated based the planar homography.

The transformation $ML_G$ is determined by the kinematic chain of the X-ray tube system. In the case of Siemens Ysio X-ray system, it comprises separate horizontal and vertical rotational joints and 3 degrees of freedom translational control. Therefore, the transformation can be decomposed as follows:

$$M_{LG} = M_V M_H = \begin{bmatrix} R_V & t_a \\ 0 & 1 \end{bmatrix} \begin{bmatrix} R_H & t_b \\ 0 & 1 \end{bmatrix}, \quad (5)$$

where $R_V$, $R_H$ are the 3×3 rotation matrix determined by the angles of the vertical rotation joint and horizontal joint, respectively; $t_a$ is the 3×1 translation vector determined by the translational control parameter, and $t_b$ is the fixed 3×1 translation vector between the two rotational joints. These matrices and vectors can be derived from the current tube control parameters according to the manufacturer's mechanical specification.

Given a set of N images of the detector 210 taken by the 3D camera 204 at various tube poses, the optimal $M_{DG}$ and $M_{CL}$ can be obtained by minimizing 3D point alignment errors based on the two paths of transferring a point from the detector 210 to the global coordinate system (X, Y, Z) in Eq. (3). That is, $$M_{CL}^*, M_{DG}^* = \operatorname{argmin}_{M_{CL}^*, M_{DG}^*} \Sigma_{i=1}^N \Sigma_k \| M_{LG}^i M_{CL} M_{DC}^i P_D^k \|^2, \quad (6)$$

where $M_{LG}^i$ and $M_{DC}^i$ are the transformations from the tube collimator coordinate system to the global tube coordinate system (X, Y, Z), and from the detector coordinate system 211 to the 3D camera coordinate system 205, respectively, for the i-th image. The optimization of Eq. (6) can be carried out by using non-linear least squares solvers such as Ceres Solver open source C++ library.

With these two transformations, two tasks are performed:

(1) Body landmark detection and region segmentation: This is done by first transferring the patient point cloud from the 3D camera coordinate system 205 to the detector coordinate system 211 via the transformations (1) from the 3D camera coordinate system 205 to the tube collimator coordinate system, (2) from the tube collimator coordinate system to the global tube coordinate system (X, Y, Z), and (3) from the inverse of the transformation from the detector coordinate system 211 to the global tube coordinate system (X, Y, Z). That is, $$M_{CD} = M_{DG}^{-1} M_{LG} M_{CL} \quad (7)$$

(2) Automatic tube control: Any point $P_C$ in the 3D camera coordinate system 205 can first be transformed to the global tube coordinate system (X, Y, Z) via the current tube control parameters:

$$P_G = M_{LG} M_{CL} P_C. \quad (8)$$

Then the optimal tube control parameters are estimated, such that the light field emitted from the collimator center is centered at the point of interest:

$$M_{LG}^* = \operatorname{argmin}_{M_{LG}} \| M_{LG} P_L - P_G \|_2, \quad (9)$$

where the point $P_L$ is the desired light field center in the tube collimator coordinate system. The optimal $M_{LG}^*$ transformation can be calculated by non-linear least squares and the corresponding tube control parameters can be derived based on inverse kinematics of the tube robotic system's mechanical kinematic chain.

Patient Surface Estimation

In some embodiments, the system and method include automatic generation of a personalized 3D mesh model ("avatar") of a person from an image obtained using a 3D camera 204. Embodiments of the system and method provide a visual understanding of the personalized mesh generation method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, some embodiments are performed within a computer system using data stored within the computer system. Other embodiments perform a subset of the functions discussed herein using application specific integrated circuitry (ASIC).

The personalized 3D mesh model of a person estimates the body pose as well as the shape of the person from 3D depth image data obtained from a 3D camera 204. Such a personalized 3D mesh model of a person is referred to herein as an "avatar". In some embodiments, the system and method generate an avatar from a single snapshot from the 3D camera 204, which captures a partial view of the person. The system and method can generate an avatar regardless of whether the patient is wearing clothing. Some embodiments reconstruct a detailed body shape (mesh) from a partial view of the body, including estimating body shape of a person under the clothing.

To generate an avatar of a person, the system uses a model based approach to fit a human skeleton model to depth image data of a person. The estimated pose skeleton is then used to initialize a detailed parametrized deformable mesh (PDM) that is learned in an offline training phase. During the (online) testing phase, the PDM is optimized to fit the input depth data from the 3D camera 204 by perturbing the body pose and shape to fit the PDM to the depth data. Some embodiments use this sampling based approach to accommodate clothing variations of the subject. Also, the sampling based approach accommodates bias introduced due to sensor noise.

In some embodiments, the technician first roughly estimates the patient iso-center of the scan region by observing the patient contour from profile viewpoint, and then aligns the patient iso-center approximately with the X-ray tube 202. The system and method generate an avatar that accurately fits the patient, which is then used to more accurately calculate the iso-center of the scan region. Some embodiments generate an avatar that accurately fits the patient to the depth image from the 3D camera 204, and the avatar can be used in place of the topogram to predict the position of organs in the patient's body in order to determine the scan region (ROI). This can provide a more accurate estimation of the scan range and decrease the patient's exposure to radiation.

Figure 6:
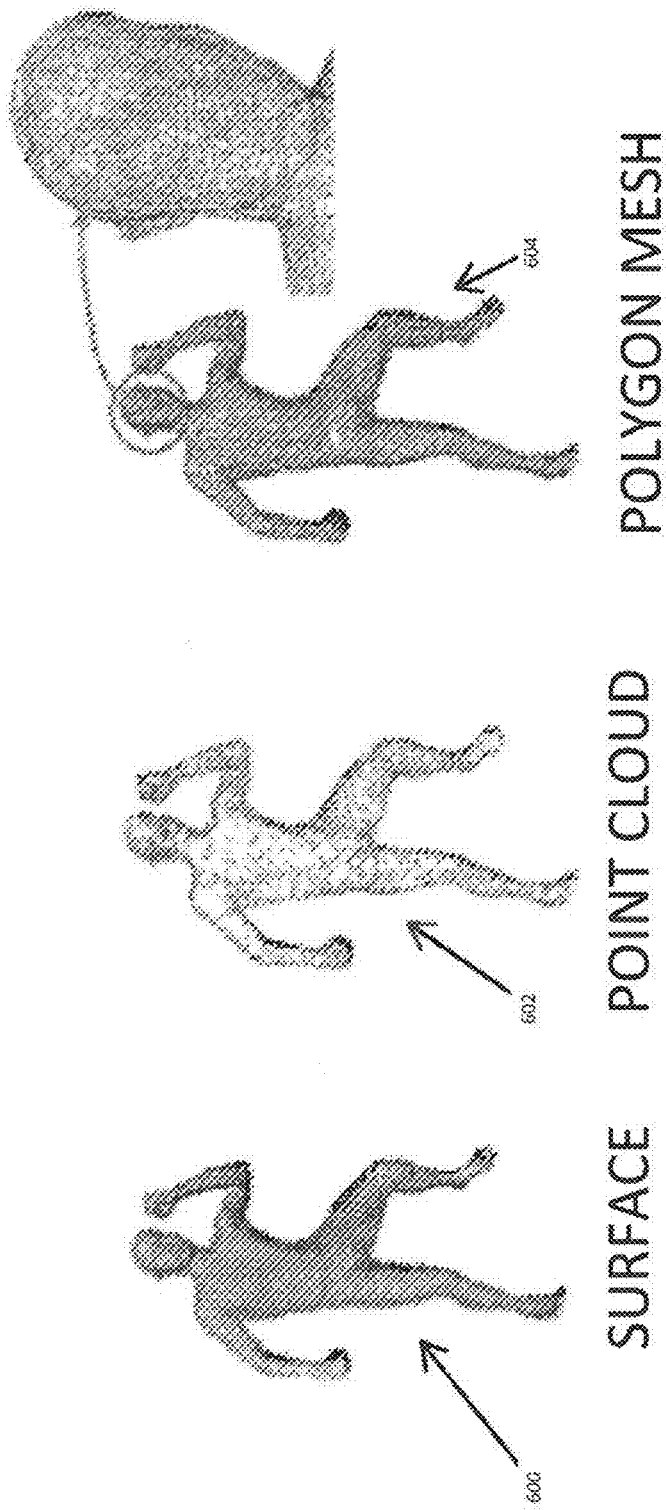
FIG. 6 shows the progression from surface model to point cloud model to polygon mesh model.

FIG. 6 illustrates an example of representing a surface using point cloud and polygon mesh. As shown in FIG. 6, human body surface 600 can be represented using a point cloud 602 and a polygon mesh 604. In computer graphics, 3D object shapes are generally represented by three-dimensional (3D) surfaces X, indicated by 600. Two popular ways to represent a 3D surface is using a point cloud 602 (generated by point sampling the surface 600) and using a polygon mesh 604 (generated by polygonal approximation of the surface 600). A point cloud 602 is generally viewed as a collection of sensor readings of the object surface 600, where each element in the cloud 602 represents the 3D coordinate of a surface point. Although point clouds may be more computationally manageable than other models, especially for complex surfaces, point clouds discard information about the surface continuity, including the topology of surface connectivity. A point cloud 602 of a surface X can be denoted as $P^X=(p_1, \ldots, p_k)$. This is a common way to represent data obtained from 3D acquisition devices, such as a 3D camera 204.

A polygon mesh 604 is a collection of vertices and edges that defines the shape of an object. A polygon mesh 604 of a surface X can be denoted as $M^X=(P^X,V^X)$, where $P^X=(p_1, \ldots, p_k)$ represents the vertices and $V^X=(v_1, \ldots, v_k)$ includes the vertex indices that define the edges of the current polygon. Triangles are commonly used as polygons in the mesh, and each triangle $t_k$ is represented using three vertices $(p_{1,k}, p_{2,k}, p_{3,k})$ and three edges $(v_{1,k}, v_{2,k}, V_{3,k})$. This disclosure is not limited to polygon meshes using triangles, and other polygons, such as tetrahedrons, can be used in a polygon mesh.

Some embodiments use a learned parametric deformable model (PDM) of the human body to generate the avatar for a patient. The PDM divides the full human body deformation into two separate deformations, pose and shape deformations, where the pose deformation can be further divided into rigid and non-rigid deformations. In some embodiments, the human body is represented using a polygon mesh 604 comprising a set of triangles Therefore, the triangles $t_k^i$ in any given mesh $M^i$ representing the human body can be represented as the triangles of a template mesh $\hat{M}$ with some deformations. The triangles in the template mesh are denoted as $\hat{t}_k$ and two edges of each triangle are denoted as $\hat{v}_{k,j}$, j=2,3. Then, the triangles in $M^i$ can be represented as:

$$v_{k,j}^i = R_{l[k]}^i S_k^i Q_k^i \hat{v}_{k,j}, \quad (10)$$

where $R_{l[k]}^i$ is the rigid rotation that has the same value for all of the triangles belonging to the same body part l, $S_k^i$ is the shape deformation matrix, and $Q_k^i$ is the pose deformation matrix.

In order to learn a pose deformation model from a set of training data, a regression is learned for each triangle $t_k$, which estimates the pose deformation matrix Q as a function of the twists of its two nearest joints $\Delta r_{l[k]}^i$, $$Q_{k,l[m]}^i = \Gamma_{a_{k,l[m]}}^T (\Delta r_{l[k]}^j) = a_{k,l[m]}^T \begin{bmatrix} \Delta r_{l[k]}^j \\ 1 \end{bmatrix}. \quad (11)$$

In the above equation, Δr can be calculated from the rigid rotation matrix R. If Q is given, the regression parameter a can be easily calculated. However, the non-rigid deformation matrix Q for each triangle is unknown. Accordingly, the deformation matrices for each of the triangles are solved by solving an optimization problem that minimizes the distance between the deformed template mesh and the training mesh data subject to a smoothness constraint. This optimization problem can be expressed as:

$$\operatorname*{argmin}_{\{Q_1^i \ldots Q_P^i\}} \sum_k \sum_{j=2,3} \| R_k^i Q_k^i \hat{v}_{k,j} - v_{k,j}^i \|^2 + w_s \sum_{k_1, k_2 adj} I(l_{k_1} = l_{k_2}) \| Q_{k_1}^i - Q_{k_2}^i \|^2, \quad (12)$$

where the first term minimizes the distance between the deformed template mesh and the training mesh data and the second term is a smoothness constraint that prefers similar deformations in adjacent triangles that belong to the same body part. $w_s$ is a weight that can be used to tune the smoothness constraint and $I(l_{k_1}=l_{k_2})$ is equal to the identity matrix I when the adjacent triangles belong to the same body part and equal to zero when the adjacent triangles do not belong to the same body part.

After training of the pose deformation model, the mesh model can be manipulated to form different body poses by initializing the rigid rotation matrix R with different values. For examples, the training poses can include a diving pose a template pose for a patient standing facing front, and a walking pose. The pose deformations can be obtained using a pose deformation model trained with a plurality of training instances having different poses.

In order to learn the shape deformation from a set of training data, principle component analysis (PCA) is employed to model shape deformation matrices as a linear combination of a small set of Eigen spaces, $$S_k^i = F_{U_k, \mu_k}(\beta_k^i) = U_k \beta_k^i + \mu_k. \quad (13)$$

In equation (4), F is the function of PCA coefficient β, μ is the mean vector, and U is the eigenvector of the data when doing the PCA dimension reduction. Similar to the pose estimation, the shape deformation matrix S for each triangle is unknown. Again, an optimization problem that minimizes the distance between the deformed template mesh and the training mesh data subject to a smoothness constraint is used to estimate the matrix S:

$$\underset{S^i}{\operatorname{argmin}} \sum_k \sum_{j=2,3} \| R^i_k Q^i_k \hat{v}_{k,j} - v^i_{k,j} \|^2 + w_s \sum_{k_1,k_2 adj} \| S^i_{k_1} - S^i_{k_2} \|^2, \quad (14)$$

where the first term minimizes the distance between the deformed template mesh and the training mesh data and the second term is a smoothness constraint that prefers similar shape deformations in adjacent triangles.

Once the PCA parameters (i.e., set of eigenvectors) are obtained, the mesh model can be manipulated to form different body shapes (tall to short, underweight to overweight, strong to slim, etc.) by perturbing β. Shape deformations are obtained using a trained shape deformation model. The shape deformations obtained by PDM shape deformation along the direction of the first principal component (β). For example, deformations can include an extreme case of an underweight body shape obtained using the trained shape deformation model, the template mesh representing an average body, and an extreme case of an overweight body shape obtained using the trained shape deformation model. The shape deformations can be obtained using a shape deformation model trained with a plurality of training instances having different body shapes.

The training process to train the pose deformation model and shape deformation model for the PDM uses a large number of 3D mesh training examples. The training dataset can be built from real human models with a high-precision laser scanner that captures each person from different viewing angles. Then, a registration algorithm can to be applied to construct the full body model for each person from the partial views. Additional processing can include filling holes, removing noises, and smoothing surfaces.

Figure 9:
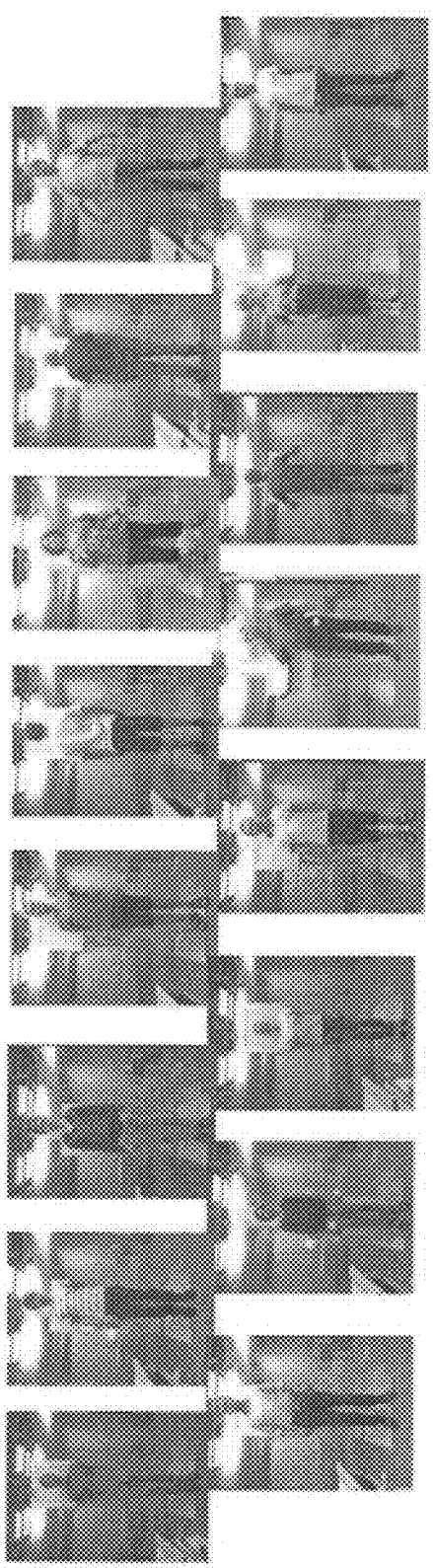
FIG. 9 is a diagram of a set of people from whom training and testing data are acquired for training and evaluation.
Figure 10:
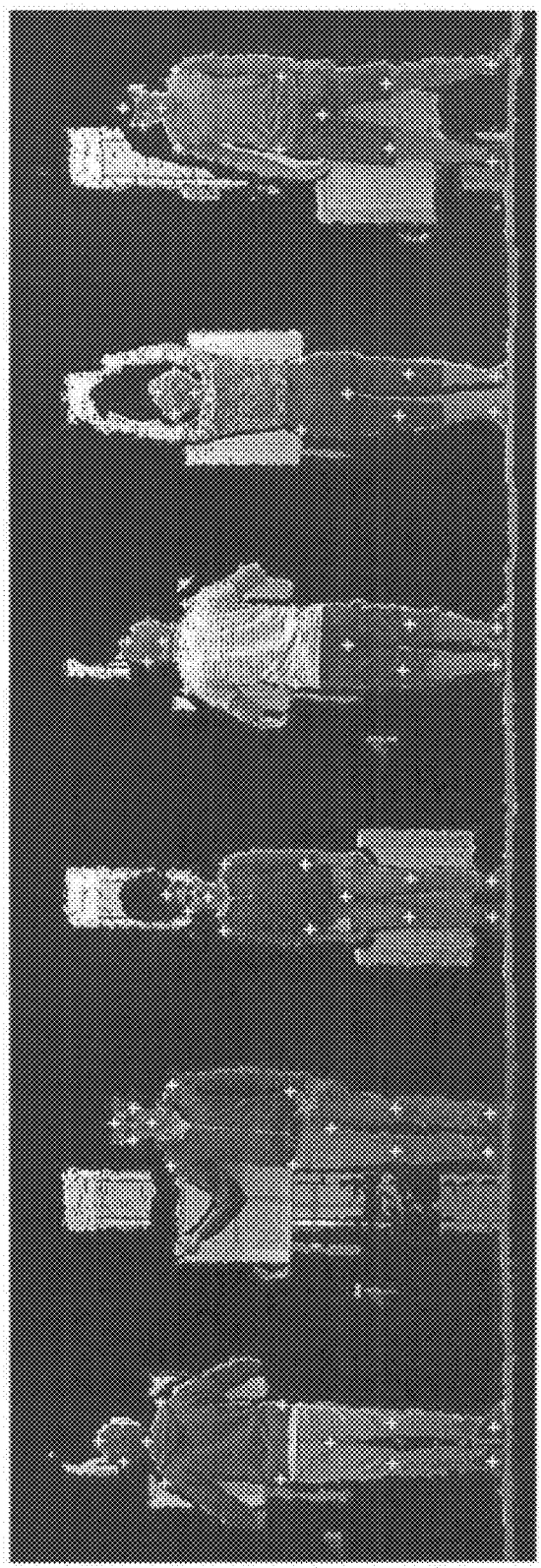
FIG. 10 is a diagram showing location of landmarks on a set of people from whom the testing data are acquired for evaluation.

FIG. 9 illustrates an exemplary dataset of people, including male, female, short, tall, thin and full-figured subjects. Images are collected in front-facing and back-facing positions. FIG. 9 include 16 people, 10 of whom were used for training. The remaining six people were used for testing/evaluation. FIG. 10 shows the results of evaluation on the people used for testing/evaluation, after completion of training. FIG. 10 shows positions of detected landmarks, indicated by plus (+) signs, on each test subject used to evaluate the patient model.

In some embodiments, "synthetic human models" are used to train the PDM. Synthetic human models can be generated from 3D commercial software. In an exemplary implementation, a 3D animation software called POSER can be used to generate synthetic human models to populate the training dataset. POSER is a 3D rendering software that can be used for posing and animation of 3D polygon meshes of humans. This software is provided with a library of pre-built human models with large freedom of joint and shape parameters. POSER can generate thousands of 3D human mesh instances with different poses and shapes in about an hour. Using POSER, all of the mesh instances originated from the same mesh template are fully labeled and registered. For example, the number of vertices in each mesh instance is the same as the template mesh and the vertex order remains the same no matter what kind of pose the mesh forms.

In some embodiments, the pose deformation model is trained with different mesh instances of the same human subject in various poses, while the shape deformation model is trained with mesh instances from many subjects in a neutral pose. Subsequently in the test phase, the gender of the test subject is known, so such decoupling is not a problem. Two separate pose deformation models (male and female) are trained and during testing, the appropriate one of the trained pose deformation models is applied when generating an avatar for a patient according to the known gender of the patient.

Among all of the training mesh instances, a person with an average or median body size and a neutral pose is selected as the template mesh. The full body of the template mesh is divided into a plurality of different body parts and a plurality of joint landmarks on the template mesh are manually selected.

In some embodiments, the template mesh is divided into 18 body parts, and 16 points on the template mesh are selected as joint landmarks. The 18 body parts (and indices used to identify the body parts) are as follows: left and right foot (0,1), left and right lower leg (2,3), left and right upper leg (4,5), pelvis (6), left and right hand (7,8), left and right forearm (9,10), left and right upper arm (11,12), abdomen (13), chest (14), left and right shoulder (15, 16), and head (17). The joint landmarks correspond to locations of various joints and other significant anatomical locations. The 16 joint landmarks (and indices identifying the landmarks) are as follows: left and right ankle (0,1), left and right knee (2,3), left and right waist (4,5), groin (6), left and right wrist (7,8), left and right elbow (9,10), left and right shoulder top (11,12), chest center (13), head bottom (14), and head top (15).

Figure 7:
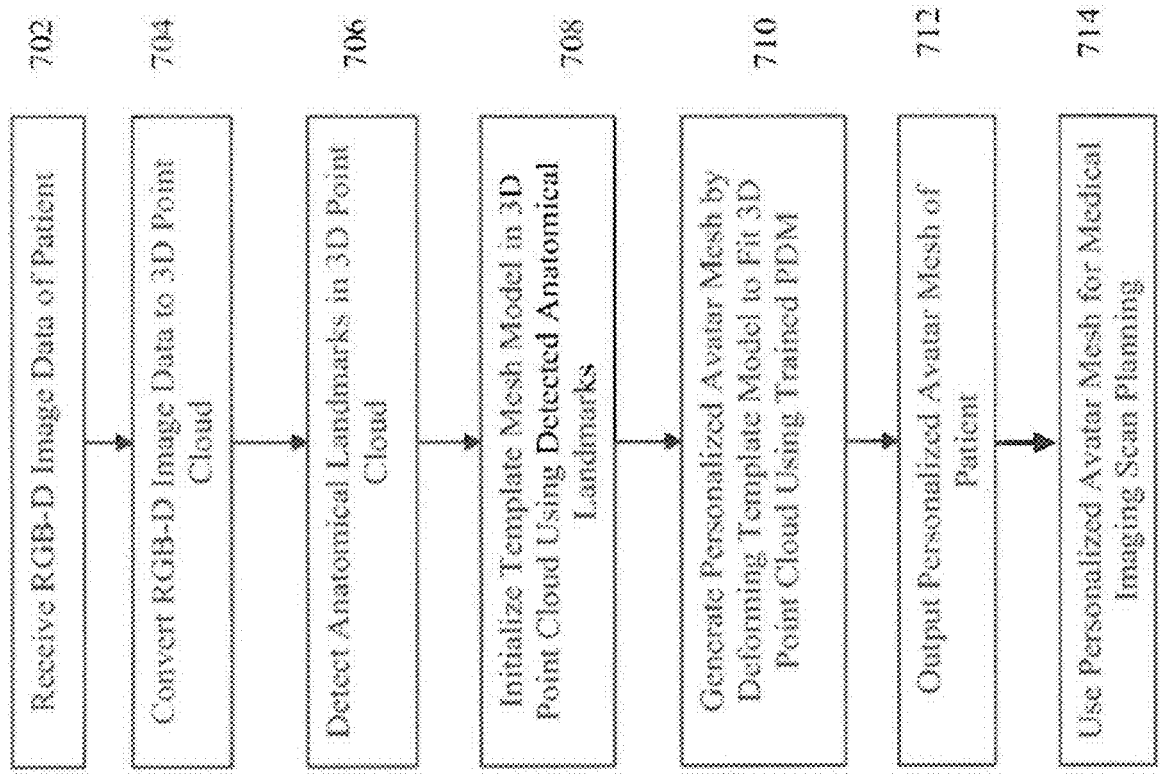
FIG. 7 is flow chart of an embodiment of the method of FIG. 5.

FIG. 7 illustrates a method of generating a personalized 3D mesh model (avatar) for a patient according to some embodiments. The method of FIG. 7 can be used as part of a scanning planning procedure to plan a scan for acquiring an X-ray image of a patient. The method of FIG. 7 assumes that the patient is standing in front of the X-ray detector 210, either facing toward or facing away from the X-ray tube 202. In some embodiments, the model assumes that the patient is covered with clothing, and applies constraints accordingly before generation of the avatar for the patient.

Referring to FIG. 7, at step 702, 3D depth image data of a patient is received from a 3D camera 204. In some embodiments, the 3D depth image data is obtained in a single snapshot from the 3D camera 204. The 3D camera 204 can be a structured light based camera (such as Microsoft Kinect or ASUS Xtion), a stereo camera, or a time of flight camera (such as Creative TOF camera). The 3D depth (RGB+Depth) image data includes an RGB image, in which each pixel has an RGB value, and a depth image, in which the value of each pixel corresponds to a depth or distance of the pixel from the 3D camera 204. Assuming the patient is in front of the X-ray detector 210 for medical image acquisition, the 3D camera 204 is appropriately positioned so it has an unobstructed view of the patient in front of the X-ray detector 210. For example, the depth camera may be mounted across from the X-ray detector 210 or on the X-ray tube 202. The 3D depth image data can be received directly from the 3D camera 204, or can be received by loading previously acquired 3D depth image data of a patient.

Returning to FIG. 7, at step 704, the 3D depth image data is converted to a 3D point cloud. In particular, the depth image of the 3D depth image data is used to map each pixel in the RGB image to a 3D location, resulting in a 3D point cloud representing the patient.

At step 706, anatomical landmarks are detected in the 3D point cloud. In particular, each of the joint landmarks selected in the template mesh is detected in the 3D point cloud. The joint landmarks can be detected in the 3D point cloud using trained machine learning based classifiers trained based on annotated training data.

For example, a respective probabilistic boosting tree (PBT) classifier can be trained for each of the joint landmarks and each joint landmark can be detected by scanning the 3D point cloud using the respective trained PBT classifier. In some embodiments, the relative locations of the landmarks are used in the landmark detection. For example, the trained classifiers for each of the joint landmarks can be connected in a discriminative anatomical network (DAN) to take into account the relative locations of the landmarks. In some embodiments, the trained classifiers can be applied to the 3D point cloud in a predetermined order, where each landmark that is detected helps to narrow the search range for the subsequent landmarks. In other embodiments, PBT classifiers are trained to detect a plurality of body parts (e.g., head, torso, pelvis) and the detected body parts a used to constrain the search range for the PBT classifiers used to detect the joint landmarks.

At step 708, the template mesh model is initialized in the 3D point cloud using the detected anatomical landmarks. As described above the template mesh model is a mesh selected from the meshes in the training dataset that has a mean or median body size and a neutral pose. The template mesh model is divided into a plurality body parts and a corresponding location for each of the plurality joint landmarks on the template mesh is stored. The template mesh is initialized in the 3D point cloud by calculating a rigid transformation of the template mesh to the 3D point cloud that minimizes error between the detected locations of the joint landmarks in the 3D point cloud and the corresponding locations of the joint landmarks in the template mesh. This rigid transformation provides and initial rigid rotation matrix R, which when applied to the template mesh results in an initialized avatar.

At step 710, a personalized avatar mesh is generated by deforming the template mesh to fit the 3D point cloud using the trained parametric deformable model (PDM). As described above, the PDM is trained offline by training a pose deformation model and a shape deformation model from the training data. In step 710, the trained PDM is directly applied to the task of data completion. Given the 3D point cloud and the joint landmarks, the PDM can generate a realistic full 3D mesh output that is consistent with the partial data by minimizing the objective function:

$$\underset{\{\beta, \Delta r, \gamma_k\}}{\operatorname{argmin}} \sum_{k} \sum_{j=2,3} \| R_k F_{U,\mu}(\beta) \Gamma_{a_k}(\Delta r_{l[k]}) \hat{v}_{k,j} - (y_{j,k} - y_{1,k}) \|^2 + w_z \Sigma_{l=1}^{L} w_l \| y_l - z_l \|^2, \quad (15)$$

where $R_k$ is the rigid rotation matrix, $F_{U,\mu}(\beta)$ is the trained shape deformation model, $\Gamma F_{a_k}(\Delta r_{l[k]})$ is the trained pose deformation model, $\hat{v}_{k,j}$ denotes edges of a triangle in the template mesh, y denotes vertices of the estimated avatar mesh model, and L is the set of correspondences between the avatar vertex $y_l$ and the corresponding point $z_l$ in the 3D point cloud Z. The first term of this objective function defines the mesh output to be consistent with the learned PDM model and the second term regulates the optimization to find the set that best fits the input point cloud. To balance the importance of the two terms, a weighting term $w_z$ is applied.

The PDM utilized in some embodiments adds another weight term $w_l$ in Equation (6). The input is from a 3D camera sensor, so the data accuracy may be affected by the actual distance between the depth camera sensor and each point. Accordingly, the present inventors have created a noise model to simulate the effects of distance from the depth camera on the accuracy of the points in the 3D point cloud. The noise model generates a different value of $w_l$ for each registered point (e.g., each joint landmark) based on a distance of each joint landmark from the 3D camera 204.

In Equation (6) there are three parameter sets (R, Y, and β) to be optimized. This forms a standard non-linear and non-convex optimization problem. In order to avoid the possibility of converging to a sub-optimal solution, some embodiments use an iterative process to optimize the three parameters. In particular, the three sets of parameters are treated separately, optimizing only one of them at a time while keeping the other two fixed. In some embodiments, a three-step optimization can be performed as follows:

Optimize R with S and Y fixed, then update ΔR and Q accordingly;

Optimize Y with R and S fixed; and

Optimize S with R, Q, and Y fixed.

In step (1) of three-step optimization procedure, the rigid rotation matrix R is optimized using Equation (6) while the shape deformation S and the vertices Y of the estimated avatar mesh model are fixed. This results in an updated value of Δr for each triangle in the estimated avatar mesh model and the pose deformation Q for each triangle is updated based on the updated Δr using the trained posed deformation model $\Gamma_{a_k}(\Delta r_{l[k]})$. Accordingly, step (1) of the optimization procedure optimizes the pose of the estimated avatar model. In step (2) of the three-step optimization procedure, the locations of the vertices Y of the estimated avatar mesh are optimized using Equation (6) while the shape deformation S and rigid rotation matrix R (and pose deformation) are fixed. This step is a fine-tuning step that adjusts the locations of the vertices Y to better match the 3D point cloud. In step (3) of the optimization procedure, the shape deformation S is optimized using Equation (6) while the rigid rotation matrix R, the pose deformation Q, and the vertices Y of the estimated avatar mesh are fixed. In particular, first principal component β is adjusted to find the shape deformation calculated using the trained deformation model $F_{U,\beta}(\beta)$ that minimizes the objective function in Equation (6). Accordingly, the three-step optimization procedure first finds an optimal pose deformation, then performs fine-tuning adjustments of the vertices of the estimated avatar model, and then finds an optimal shape deformation. This three-step optimization procedure can be iterated a plurality of times. For example, the three-step optimization procedure can be iterated a predetermined number of times or can be iterated until it converges.

The second term in Equation (6) requires finding correspondences between the 3D point cloud and landmarks on the 3D mesh model. In the method of FIG. 7, we first estimate an initial R based on the detected joint landmarks in the 3D point cloud (step 708). Then, the above three-step optimization procedure is iterated a plurality of times to get a current estimated mesh model, $M_{curr}$, where only the joint landmarks are used to find the correspondences. For example, the three-step optimization procedure using only the joint landmarks to find the correspondences can be iterated a predetermined number of times or can be iterated until it converges. Next, a registration algorithm based on the Iterative Closest Point algorithm can be performed to obtain a full registration between the 3D point cloud and the current 3D mesh model $M_{curr}$. Once the registration between the 3D point cloud and the current 3D mesh model $M_{curr}$ is performed, correspondences between corresponding pairs of points in the 3D point cloud and the current 3D mesh model that have a distance ($\|y_l - z_l\|$) larger than a predetermined threshold are removed. The remaining correspondences are then used to estimate a new rigid rotation matrix R, and the three-step optimization procedure is repeated. This optimization-registration process is iterated until convergence.

The optimization procedure described above for partial data completion using the trained PDM generates a 3D avatar that closely fits to the actual pose and shape of the patient. Since the template avatar is generated from PSOER in a naked condition, but the 3D point cloud is captured from a real patient who is typically wearing clothes, solving Equation (6), which minimizes the differences between the avatar mesh surface and the 3D point cloud, may result in errors. In some embodiments of the present system and method, an optimization method that accommodates the clothing is utilized.

To account for clothing worn by the patient, some embodiments search for an avatar having vertices that are all beneath the input 3D point cloud to some degree. To that end, a clothing constraint $d_{cloth}$ can be defined as:

$$d_{cloth}(y) = \Sigma_{l \in L} \| \in_1 + n_{z_l}^T (z_l - y_l) \|^2 \quad (16)$$

where L is the set of correspondences between the avatar vertex $y_l$ and the corresponding point $z_l$ in the 3D point cloud, and $n_{z_l}$ is the normal of the point $z_l$. The avatar mesh is below the 3D point cloud when $n_{z_l}^T(z_l - y_l) > 0$, $\forall l \in L$. The term $\in_l \leq 0$ ensures that the avatar mesh lies sufficiently below the input 3D point cloud within the clothing region while the avatar overlaps with the input 3D point cloud in the non-clothing region. The value of E is determined by:

$$e_k = (1 - P(y_k))\tau, \quad (17)$$

where $k \in X$, $P(y_k)$ represents the probability that an avatar vertex $y_k$ belongs to a non-clothing region. The probability $P(Y)$ is calculated using a trained probability model that is learned statistically from ground truth training data. The threshold T represents the maximal distance between the avatar surface and the clothing surface, including the thickness of the clothing. It is to be understood that the clothing constraint can be applied, not just for clothing, but for anything covering the patient, such as a radiation protector, blankets, pillows, etc. Since what is covering the patient can be known as a prior, different probability models can be trained for different patient coverings (e.g., clothing, radiation protector, blanket, etc.), and the threshold T can be adjusted based on what is covering the patient.

Since, in an advantageous embodiment, the input 3D point cloud data is generated from 3D depth image data collected from the patient lying on a table, another constraint $d_{table}$, referred to herein as the table constraint, can be utilized to specify that all vertices of the avatar mesh should be above the table. In particular, we attempt to minimize:

$$d_{table}(y) = \Sigma_{k \in X, y_k^z < h_{table}} \| \in_{table} + y_k^z - h_{table} \|^2, \quad (18)$$

where $y_k^z$ is the z-axis value (perpendicular to the surface of the table) of the avatar vertex $y_k$, $h_{table}$ is the current table height (which is known), and the term $e_{table}$ ensures that the avatar mesh lies sufficiently above the table.

The above equations have many solutions. To achieve an avatar mesh that is deformed plausibly, the solution can be regularized with a smoothing term, which minimizes:

$$s(y) = \sum_{k \in K} \| (y_k - \hat{y}_k) - \frac{1}{[N_k]} \sum_{j \in N_k} (y_j - \hat{y}_j) \|^2, \quad (19)$$

where y denotes the vertices of the new avatar mesh, $\hat{y}$ denotes the vertices of the current avatar mesh, and $N_k$ is the set of vertices adjacent to the vertex $y_k$. This regularization prefers a deformation of a vertex that is similar to the average deformation of its neighboring vertices.

According to an embodiment of the present invention, the above described constraints can be combined to get an optimization function that minimizes:

$$E[Y] = \Sigma_k \Sigma_{j=2,3} \| R_k F_{U,\mu} \Gamma_{a_k} \hat{v}_{k,j} - (y_{j,k} - y_{1,k}) \|^2 + d_{cloth}(Y) + d_{table}(Y) + d_{table}(Y) + s(Y), \quad (20)$$

where first term is the same as the first term in Equation (6), the second term is the clothing constraint $d_{cloth}(Y)$, the third term is the table constraint $d_{table}(Y)$, and the fourth term is the smoothing constraint $s(Y)$. The cost function can be used in place of the cost function expressed in Equation (6) to optimize the parameter sets (R, Y, and β). In particular, the iterated optimization-registration process described above (including the iterated three-step optimization procedure) can be used to find the optimal parameters to minimize the cost function of Equation (20). This procedure is iterated until convergence, resulting in a 3D personalized avatar mesh for the patient.

Referring again to FIG. 7, at step 712, the 3D personalized avatar mesh for the patient is output. For example the 3D personalized avatar mesh can be output by displaying the 3D personalized avatar mesh on a display screen of a computer system.

At step 714, the avatar of the patient is used for medical imaging scan planning. In some embodiments, the avatar can predict locations of the patient's bones. For example, an atlas of organs can be aligned with the avatar for the patient and superimposed on the patient body. This can assist an operator in specifying an ROI. The avatar of the patient can be used in place of a topography scan. Since the avatar accurately fits to the patient, the iso-center of the scan can also be estimated from the avatar with minimum error.

Some embodiments take prior knowledge into account and use machine learning to estimate the patient surface geometry with a high accuracy, while being fast enough for a seamless integration in the patient scanning workflow.

Figure 5:
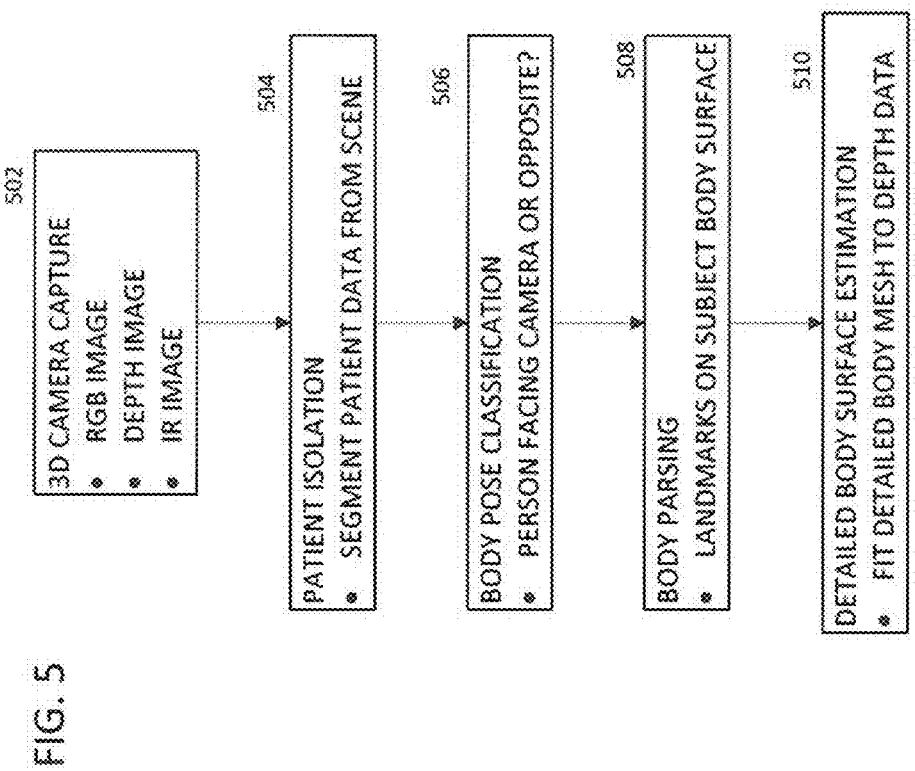
FIG. 5 is a flow chart of a method of using machine learning to determine the standing patient surface geometry of the patient of FIG. 4.

FIG. 5 shows a method for patient surface estimation. Referring to FIG. 5, at step 502, the 3D depth image data of the patient is captured using the 3D camera 204. This 3D depth image data can be the same 3D depth image data received in step 102 of FIG. 1. Alternatively, if once the pose of the 3D camera 204 is estimated with respect to the coordinate system 211 of the X-ray detector 210, it is determined that the original 3D depth image acquired in step 102 does not contain sufficient anatomy of the patient, the X-ray tube 202 on which the 3D camera 204 is mounted can be repositioned so more of the patient's anatomy is in the field of view of the 3D camera 204, and a new 3D depth image can be acquired. The 3D depth image includes an RGB image and a depth image. The color data in the RGB image and the depth (range) data in the depth image can be combined to represent the 3D depth image data of the patient as a 3D point cloud.

Given the color and depth data represented as a 3D point cloud, an image region containing only the patient and the X-ray detector 210 is localized. The relative position of the 3D camera 204 with respect to the X-ray tube 202 is known, as it is established during the calibration process, and the range of X-ray detector 210 movement is limited. In some embodiments, the calibration is performed with respect to the X-ray detector stand 212, which remains stationary, even when the X-ray detector 210 moves up and down. This information is used as a spatial prior to automatically crop the image region enclosed by the 3D volume containing the patient and the X-ray detector 210. This cropped data is then transformed such that the z-axis is aligned with the X-ray detector 210 surface normal and the x-y plane is aligned with the X-ray detector 210 surface. The transformed depth data (and associated color information) is then orthogonally projected on the x-y plane to generate a color and depth image pair referred to herein as the re-projected image, which is then used for subsequent processing. Next, to further refine the position and extent of the patient in front of the X-ray detector 210, a machine-learning based full body detector 210 can be applied on the re-projected image to detect an estimate of the patient position in the re-projected image. For this patient fully body detection, a Probabilistic Boosting Tree (PBT) with 2D Haar features extracted over re-projected depth and surface normal data can be trained and used as the full body detector 210. The PBT is trained using features extracted from annotated training data and the trained PBT is used to detect a coarse positon of the patient in the re-projected image.

At step 504, pose detection is performed on the re-projected image to classify a pose of the patient. Given the coarse patient position information, the patient pose can be classified as facing front (i.e., patient facing the X-ray tube 202 and 3D camera 204) or facing back (i.e., patient facing the X-ray detector 210) using one or more machine-learning based pose classifiers. Each of the pose classifiers can be a trained PBT classifier. According to some embodiments, the PBT framework can be extended to multiple channels by considering Haar features extracted from the re-projected depth image, surface normal data, a saturation image, as well as U and V channels from LUV space. Fusing multiple channels can provide a significant improvement in pose detection over using depth information only.

In some embodiments, a facing-front versus facing-back classifier is applied to the re-projected image by considering half of the patient region that is close to the sensor (3D camera 204). This region covers the front of the body for the front-facing case and the back of the body for the back-facing case. In other embodiments, instead of training a single multi-class classifier for pose detection, multiple binary classifiers can be trained to systematically handle the data variations.

At step 508, landmark detection (body parsing) is performed. Given the patient pose information, a sparse body surface model including a plurality of anatomical landmarks is fit to the re-projected image data. The body surface model can be represented as a Directed Acyclic Graph (DAG) over the anatomical landmarks on the body surface, where the graph captures the relative position of the landmarks with respect to each other. In an advantageous embodiment, the patient surface is modeled using 10 body landmarks—head, groin, and left and right landmarks for shoulders, waist, knees, and ankles. Respective landmark detectors are trained for each of the landmarks. For example, for each landmark, a multi-channel PBT classifier with Haar features extracted from the same channels as used to train the pose classifiers (e.g., re-projected depth image, surface normal data, saturation image, and U and V channels from Luv space) can be used to train each landmark detector. Due to camera and body surface angle, as well as sensor noise, the image statistics vary significantly over the body surface.

The relative position of the landmarks is modeled as a Gaussian distribution whose parameters are obtained from annotations over a training data set. During landmark detection on the re-projected image, the trained landmark detectors are applied sequentially while taking contextual constraints of the neighboring landmarks into account. For each landmark, position hypotheses are obtained based on the trained landmark detector response as well as from previously detected landmarks in the DAG. In an exemplary implementation, given the position information for the patient, the groin landmark detection is performed first by applying the groin landmark detector in a center region of the patient. Next the knee landmark detectors are applied on an image region estimated based on constraints from the pose information as well as relative position information from the hypotheses from the groin region. One by one, landmark hypotheses are obtained for each landmark traversing the DAG.

At step 510, after all the landmark hypotheses for all the landmarks are obtained, a global reasoning is performed on the landmark hypotheses to obtain a set of landmarks with the highest joint likelihood based on the trained landmark detectors as well as the contextual information in the DAG. This sequential process of landmark detection handles the size and scale variations across patients of different ages. Once the final set of landmarks is detected using the global reasoning, body regions of the patient in the re-projected image can be defined based on the set of landmarks. For example, the re-projected image can be divided into body regions of head, torso, pelvis, upper leg, and lower leg. In a possible implementation, a human skeleton model can be fit the re-projected depth image based on the detected landmarks.

Figure 8:
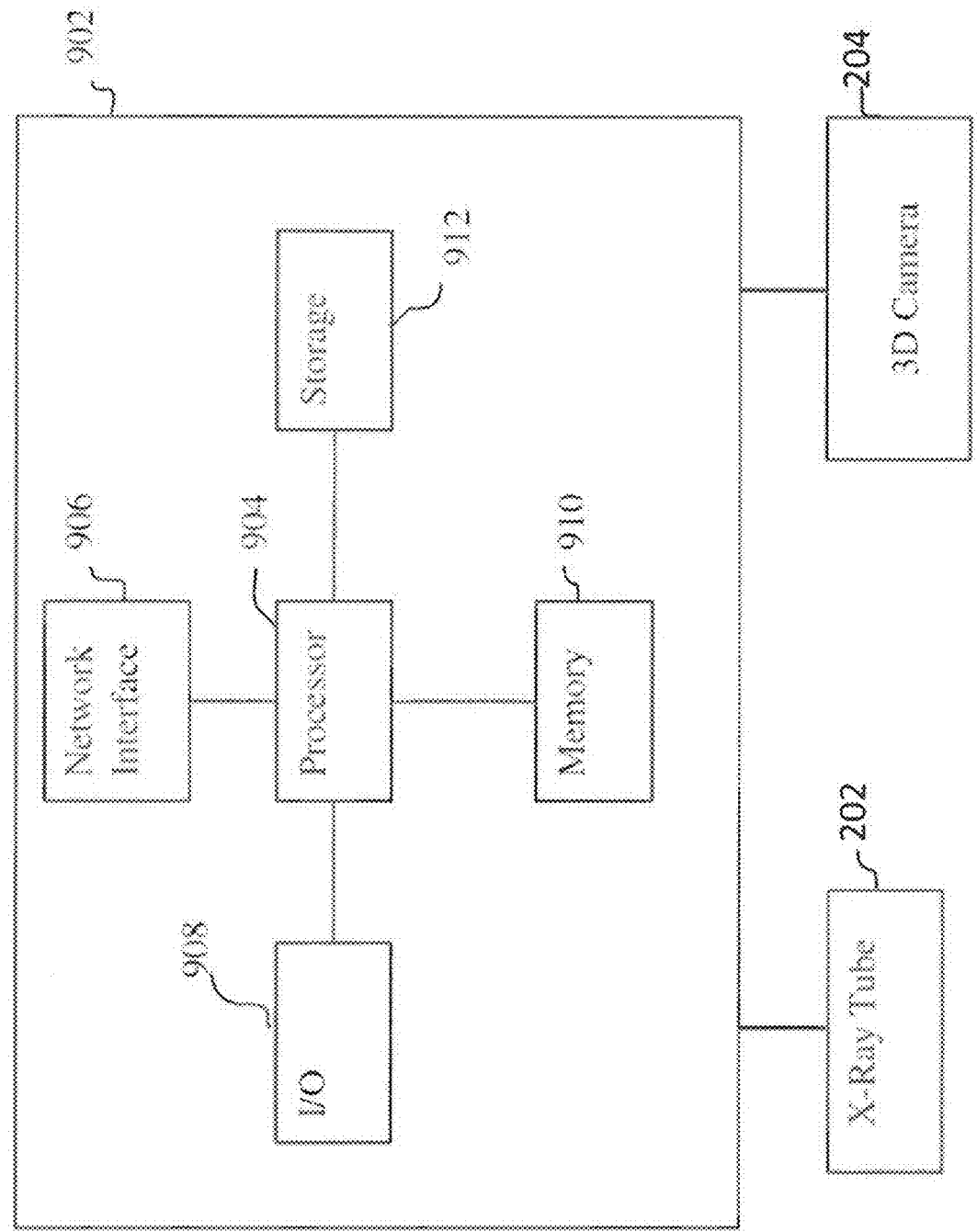
FIG. 8 is a block diagram of a system for acquiring and processing X-ray image data including the X-ray acquisition system of FIG. 2A.

The above-described method for X-ray tube scanner automation using a 3D camera 204 can be implemented on a computer using computer processors, memory units, storage devices, computer software, and other processing components. A high-level block diagram of such a computer is illustrated in FIG. 8. Computer 902 contains a processor 904, which controls the overall operation of the computer 902 by executing computer program instructions which define such operation. The computer program instructions are stored in a storage device 912 (e.g., memory, optical storage, magnetic disk) and loaded into memory 910 when execution of the computer program instructions is desired. Thus, the steps of the methods of FIGS. 1 and 5 may be performed by the computer program instructions stored in the memory 910 and/or storage 912 and controlled by the processor 904 executing the computer program instructions.

A 3D camera 204 can be connected to the computer 902 to input 3D depth image data to the computer 902. The 3D camera 204 and the computer 902 can be directly connected or communicate wirelessly through a network or other wireless communication protocol. An X-ray tube scanner 202 can also be connected to the computer 902. The X-ray tube scanner 202 and the computer 902 can be directly connected or communicate through a network or other wireless communication protocol.

Some embodiments implement the medical image acquisition system 200 and the computer 902 as one device. The computer 902 can communicate with the X-ray tube scanner 202 to control the positioning and orientation of the X-ray tube 202 and to control X-ray image acquisition by the X-ray tube 202. X-ray images acquired by the X-ray tube scanner 202 can be input to the computer 902. The computer 902 also includes one or more network interfaces 906 for communicating with other devices via a network. The computer 902 also includes other input/output devices 908 that enable user interaction with the computer 902 (e.g., display, keyboard, mouse, speakers, buttons, etc.). Such input/output devices 908 may be used in conjunction with a set of computer programs as an annotation tool to annotate volumes received from the image acquisition device 920. One skilled in the art will recognize that an implementation of an actual computer could contain other components as well, and that FIG. 9 is a high level representation of some of the components of such a computer for illustrative purposes.

Based on the estimated patient surface, the X-ray tube 202 is appropriately moved such the region of interest on the patient body scan be x-rayed. For instance, if a patient has a shoulder scan, the operator would simply select the "shoulder organ program" and the X-ray tube 202 would be positioning automatically to ensure a high quality scan.

Results

To validate the performance of this approach, data were collected using an ASUS Xtion Pro depth sensor mounted on the X-ray tube 202 of Siemens' Ysio Max scanner. The sensor was calibrated. The dataset included 16 volunteers (with varying height, gender and size); out of this sample, data from 10 volunteers was used for training and rest of testing. FIG. 3 shows sample images from the dataset.

The methods and system described herein may be at least partially embodied in the form of computer-implemented processes and apparatus for practicing those processes. The disclosed methods may also be at least partially embodied in the form of tangible, non-transitory machine readable storage media encoded with computer program code. The media may include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods may also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods may alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which may be made by those skilled in the art.

What is claimed is:

1. A method comprising:
receiving range data of a subject from a range sensor, where the range sensor is movable with an X-ray tube, and the subject is standing between the X-ray tube and an X-ray detector;
computing a surface model of the subject from the 3D depth image using a parametric model, wherein at least one parameter of the parametric model is estimated by machine learning;
selecting the region of interest of the subject based on the surface model; and
automatically controlling the X-ray tube to transmit X-ray radiation to a region of interest of the subject while the subject is standing between the X-ray tube and the X-ray detector.

2. The method of claim 1, wherein the range sensor includes a three-dimensional (3D) camera and the range data includes a 3D depth image.

3. A method comprising:
receiving range data of a subject from a range sensor, where the range sensor is movable with an X-ray tube, and the subject is standing between the X-ray tube and an X-ray detector;
computing a surface model of the subject from the 3D depth image using a parametric model, wherein at least one parameter of the parametric model is estimated by machine learning;
selecting the region of interest of the subject based on the surface model; and
automatically controlling the X-ray tube to transmit X-ray radiation to a region of interest of the subject while the subject is standing between the X-ray tube and the X-ray detector;
wherein computing the surface model from the 3D depth image of the subject comprises:
transforming a 3D point cloud representation of the 3D depth image to align the 3D depth image with a predetermined field of view of the X-ray detector using an estimated transformation between a coordinate system of the 3D camera and a coordinate system of the X-ray detector;
projecting the 3D point cloud representation to generate a re-projected image comprising a color and depth image pair; and
estimating the surface model using the re-projected image.

4. A method comprising:
receiving range data of a subject from a range sensor, where the range sensor is movable with an X-ray tube, and the subject is standing between the X-ray tube and an X-ray detector;
computing a surface model of the subject from the 3D depth image using a parametric model, wherein at least one parameter of the parametric model is estimated by machine learning;
selecting the region of interest of the subject based on the surface model; and
automatically controlling the X-ray tube to transmit X-ray radiation to a region of interest of the subject while the subject is standing between the X-ray tube and the X-ray detector;
wherein computing the surface model from the 3D depth image of the subject comprises:
detecting a body pose in the 3D depth image using one or more machine learning-based pose classifiers; and detecting anatomical landmarks of the subject in the 3D data based on the detected patient pose.

5. The method of claim 2, further comprising computing a collimation of the X-ray radiation based on the parametric model.

6. The method of claim 2, further comprising selecting a dose of the X-ray radiation based on the parametric model.

7. The method of claim 2, further comprising computing a transformation between a coordinate system of the 3D camera and a coordinate system of an X-ray detector.

8. The method of claim 2, wherein the 3D camera is mounted to the X-ray tube.

9. The method of claim 1, wherein the X-ray detector is arranged parallel to a coronal plane of the subject during the step of automatically controlling the X-ray tube.

10. A system comprising:
a movable X-ray tube scanner;
a range sensor movable with the X-ray tube scanner;
an X-ray detector positioned to detect X-rays from the X-ray tube passing through a standing subject between the X-ray tube and the X-ray detector;
a processor configured for automatically controlling the X-ray tube scanner to transmit X-rays to a region of interest of the patient while the subject is standing between the X-ray tube and the X-ray detector; and
a non-transitory, machine-readable storage medium storing a parametric deformable model, wherein the processor is also configured for estimating a surface model of the subject based on the parametric deformable model and a 3D depth image of the subject captured by the range sensor while the subject is standing between the X-ray tube and the X-ray detector, wherein at least one parameter of the parametric deformable model is estimated by machine learning.

11. The system of claim 10, wherein the range sensor is a 3D camera.

12. The system of claim 11, wherein the 3D camera is a 3D depth camera.

13. The system of claim 10, wherein the X-ray detector is mounted on a stand above a floor and is oriented to receive X-rays traveling in a horizontal direction.

14. The system of claim 13, wherein the X-ray detector is mechanically movable in a vertical direction relative to the stand.

15. The system of claim 14, wherein the processor is configured to control the X-ray tube scanner and the X-ray detector to move so that the X-ray tube scanner, the region of interest, and the X-ray detector are aligned along a line.

16. The system of claim 10, wherein the X-ray tube scanner is mechanically mounted for translating in three orthogonal dimensions and rotating in at least two orthogonal dimensions.

* * * * *